United States Patent [19]

Mues et al.

[11] 4,053,296
[45] Oct. 11, 1977

[54] FERROCENE DERIVATIVE FOR SUPPLYING PLANTS WITH IRON

[75] Inventors: Volker Mues, Wuppertal; Johannes Niggemann, Leverkusen, both of Germany

[73] Assignee: Bayer Aktiengesellschaft, Leverkusen, Germany

[21] Appl. No.: 721,736

[22] Filed: Sept. 9, 1976

[30] Foreign Application Priority Data

Oct. 2, 1975   Germany .............................. 2543999

[51] Int. Cl.$^2$ .......................... C05D 9/02; C05F 11/10
[52] U.S. Cl. ......................................... 71/1; 71/64 C; 71/DIG. 2
[58] Field of Search ...................... 71/1, 11, 27, 64 C, 71/97, DIG. 1, DIG. 2; 260/439 R

[56] References Cited

U.S. PATENT DOCUMENTS

| | | | |
|---|---|---|---|
| 2,673,213 | 3/1954 | Bersworth | 71/DIG. 2 |
| 2,891,854 | 6/1959 | Kroll | 71/1 |
| 2,921,847 | 1/1960 | Knell et al. | 71/DIG. 2 |
| 2,943,100 | 6/1960 | Holstein | 71/1 |
| 3,008,816 | 11/1961 | Hemwell | 71/DIG. 2 |
| 3,152,155 | 10/1964 | Langer | 71/1 |
| 3,711,525 | 1/1973 | Hennart | 71/97 |
| 3,728,365 | 4/1973 | Mrowca | 71/97 |
| 3,742,002 | 6/1973 | Ohlson et al. | 71/97 |
| 3,758,540 | 9/1973 | Martell | 71/DIG. 2 |
| 3,782,917 | 1/1974 | Mrowca | 71/97 |
| 3,981,712 | 9/1976 | Petree | 71/1 |

FOREIGN PATENT DOCUMENTS

| | | | |
|---|---|---|---|
| 593,470 | 3/1960 | Canada | 71/1 |
| 785,024 | 10/1957 | United Kingdom | 71/1 |
| 785,025 | 10/1957 | United Kingdom | 71/1 |

*Primary Examiner*—Wilbur L. Bascomb, Jr.
*Assistant Examiner*—Ernest G. Therkorn
*Attorney, Agent, or Firm*—Burgess, Dinklage & Sprung

[57] ABSTRACT

Ferrocene derivatives of the formula

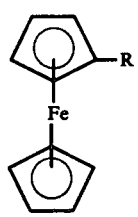

(I)

in which
R represents the group COOR$^1$,
in which
R$^1$ represents hydrogen, alkyl, one equivalent of an alkali metal, alkaline earth metal or heavy metal cation, or an ammonium cation in which one or more hydrogen atoms can be replaced by alkyl,
or R represents the group COR$^2$
in which
R$^2$ represents optionally substituted alkyl, optionally substituted alkenyl, optionally substituted cycloalkyl, optionally substituted cycloalkenyl or optionally substituted phenyl,
or
R represents the group

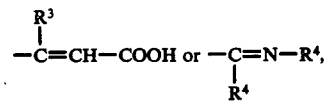

in which
R$^3$ represents hydrogen or alkyl and
R$^4$ represents a ureido or thioureido radical, a radical of the formula —CH$_2$—CH$_2$—N=CH—ferrocene, a 5-membered or 6-membered heterocyclic radical or a group of the formula —OR$^5$ or —NH-R$^6$,
in which
R$^5$ represents hydrogen, alkyl, one equivalent of an alkali metal or alkaline earth metal cation, or an ammonium cation in which one or more hydrogen atoms canbe replaced by alkyl, and
R$^6$ represents aryl or a 5-membered or 6-membered heterocyclic radical,
or
R represents the sulfonamide group or the radical —SO$_3$R$^7$,
in which
R$^7$ represents hydrogen, alkyl, one equivalent of an alkali metal or alkaline earth metal cation, or an ammonium cation in which one or more hydrogen atoms can be replaced by alkyl,
or pl R represents an alkyl, aralkyl or aryl radical which can be substituted by hydroxyl, cyano, COOR$^1$
or

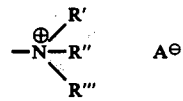

in which
R$^1$ has the above-mentioned meansing,
R', R" and R''', independently of one another, each represent hydrogen or alkyl and
A$^-$ represents halide or methosulfate, are outstandingly effective for supplying plants with the micronutrient iron.

18 Claims, No Drawings

FERROCENE DERIVATIVE FOR SUPPLYING PLANTS WITH IRON

The present invention relates to the use as fertilizers of certain ferrocene compounds and to their use for the prevention and cure of iron deficiency diseases in plants.

It is known that ferrocene derivatives can be used for treating iron deficiency anemias in humans and animals and as antioxidants, anti-knock agents, additives for motor fuels and oils, color pigments, radiation absorbers, insecticides and fungicides, from British Pat. No. 898,633, U.S. Pat. Nos. 3,432,533, 3,535,356, 3,553,241 and 3,557,143, German Offenlegungsschriften (German Published Specifications) Nos. 2,107,657, 2,453,936 and 2,453,977 and U.S.S.R. Pat. No. 400,597.

Furthermore, it is known to prevent or cure iron deficiency diseases in plants by adding water-soluble iron salts, such as, for example, iron sulfate, to the substrate in which the plants grow. Using such conventional agents, it is indeed possible to supply the plants with iron in weakly acid substrates or in substrates having a neutral reaction; however, their use in soils having a weakly basic reaction suffers from considerable disadvantages. Thus, in weakly alkaline substrates, the iron ions cannot be taken up by the plants at all or can be taken up only in an insufficient amount because these ions then separate out in the form of sparingly soluble hydroxides and therefore do not contribute to plant nutrition.

Furthermore, it is known that, if needed, the plants can be supplied with iron in the form of iron chelate complexes of citric acid, gluconic acid, nitrilotriacetic acid, ethylenediaminetetraacetic acid or ethylenediamine-N,N'-di-(o-hydroxyphenyl)-acetic acid. [See "Der Vegetationsversuch" ("Vegetation Experiments") in "Methodenbuch" ("Book of Methods"), Volume VIII, Neumann Verlag, Radebeul, Berlin, 1951, 180 to 194; Plant Physiology 26, 411 (1951); Soil Science 80, 101 to 108 (1955) and "Organic Sequestering Agents", John Wiley & Sons, Inc., New York, 1959, 455 to 469].

With the aid of such iron complexes it is possible to supply the plants with iron not only in weakly acid or neutral soils but also, to a certain degree, in weakly alkaline soils because, as a result of the relatively great stability of these complexes, an undesired precipitation of the iron cations in the neutral or weakly basic medium is largely avoided. Nevertheless, the use of iron chelate complexes for the indicated purpose suffers from some disadvantages. Thus, the duration of action of iron chelate complexes of citric acid or gluconic acid is only relatively short, since these naturally occurring acids can be degraded relatively rapidly by soil microorganisms.

The iron chelate complexes of the synthetic aminopolycarboxylic acids — with the exception of the iron complex of ethylenediamine-N,N'-di-(o-hydroxyphenyl)-acetic acid, which is important for combating chlorosis — can be employed only with certain limitations in strongly alkaline soils because the stability of the complexes does not always suffice to avoid the iron cations being immobilized in the form of sparingly soluble hydroxides or oxides. A further disadvantage is that the aminopolycarboxylic acids form very stable, highly toxic and at the same time water-soluble chelate complexes with the heavy metal ions of cadmium, lead and mercury, which can be present in the soil in the form of almost insoluble compounds. Since these heavy metal ion complexes can, because of their good solubility, pass into the soil water, the use of aminopolycarboxylic acids is not safe for toxicological reasons. It is true that the iron complex of ethylenediamine-N,N'-di-(o-hydroxyphenyl)-acetic acid, as already mentioned, of practical importance in combating chlorosis; however, it is a disadvantage that this compound can be prepared only with relative difficulty and is furthermore not light-stable.

It has now been found that ferrocene derivatives, some of which are known, of the general formula

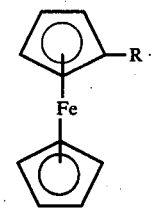
(I)

in which
R represents the group COOR¹,
in which
R¹ represents hydrogen, alkyl, one equivalent of an alkali metal, alkaline earth metal or heavy metal cation, or an ammonium cation in which one or more hydrogen atoms can be replaced by alkyl,
or
R represents the group COR²,
in which
R² represents optionally substituted alkyl, optionally substituted alkenyl, optionally substituted cycloalkyl, optionally substituted cycloalkenyl or optionally substituted phenyl,
or
R represents the group

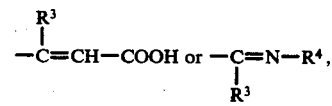

in which
R³ represents hydrogen or alkyl and
R⁴ represents a ureido or thioureido radical, a radical of the formula —CH₂—CH₂—N=CH-ferrocene, a 5-membered or 6-membered heterocyclic radical or a group of the formula —OR⁵ or —NH—R⁶,
in which
R⁵ represents hydrogen, alkyl, one equivalent of an alkali metal or alkaline earth metal cation, or an ammonium cation in which one or more hydrogen atoms can be replaced by alkyl, and
R⁶ represents aryl or a 5-membered or 6-membered heterocyclic radical,
or
R represents the sulfonamide group or the radical —SO₃R⁷,
in which
R⁷ represents hydrogen, alkyl, one equivalent of an alkali metal or alkaline earth metal cation, or an ammonium cation in which one or more hydrogen atoms can be replaced by alkyl,
or R represents an alkyl, aralkyl or aryl radical which can be substituted by hydroxyl, cyano, COOR¹ or

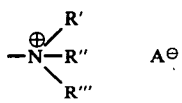

in which
R¹ has the above-mentioned meaning,
R', R" and R'", independently of one another, each represent hydrogen or alkyl and
A⁻ represents halide or methosulfate, are very suitable for supplying plants with the micro-nutrient iron.

Accordingly, the present invention provides a method of supplying plants with the micro-nutrient iron, which comprises applying to the plants or a plant habitat a ferrocene of the formula (I) alone or in admixture with a diluent or carrier.

Preferably, in the formula (I), R represents the COOR¹ group, in which R¹ represents hydrogen, straight-chain or branched alkyl with 1 to 6 carbon atoms, one equivalent of a sodium, potassium, calcium, magnesium, manganese, copper, molybdenum, zinc or iron cation or an ammonium cation n which one or more hydrogen atoms can be replaced by alkyl with 1 to 6 carbon atoms (especially by methyl);

the COR² group, in which R² represents hydrogen, straight-chain or branched alkyl with 1 to 6 carbon atoms, straight-chain or branched alkenyl with 2 to 6 carbon atoms, cyclohexyl, cyclohexenyl or phenyl, each of the 5 last-mentioned radicals being optionally substituted by carboxyl, hydroxyl or the group CO-OX or OX, in which X represents one equivalent of a sodium, potassium, calcium, magnesium, manganese, copper, molybdenum, zinc or iron cation or represents alkyl with 1 to 4 carbon atoms;

the group —CR³=CH-COOH or —CR³=N-R⁴, in which R³ represents hydrogen or straight-chain or branched alkyl with 1 to 6 carbon atoms (especially methyl), and R⁴ represents a ureido or thioureido radical, a radical of the formula —CH₂—CH₂—N=CH-ferrocene, a 5-membered or 6-membered heterocyclic radical (such as, for example, imidazolyl, 1,2,4-triazolyl, 1,3,4-triazolyl, pyridyl, pyrimidinyl or morpholinyl), the group OR⁵, in which R⁵ represents hydrogen, straight-chain or branched alkyl with 1 to 4 carbon atoms (especially methyl or ethyl), one equivalent of a sodium, potassium or calcium cation or an ammonium cation in which one or more hydrogen atom can be replaced by alkyl with 1 to 6 carbon atoms (especially by methyl), or the group —NH-R⁶, in which R⁶ represents phenyl or a 5-membered or 6-membered heterocyclic radical (such as, for example, imidazolyl, 1,2,4-triazolyl, 1,3,4-triazolyl, pyridyl, pyrimidinyl or morpholinyl);

a sulfonamide group or the radical —SO₃R⁷, in which R⁷ represents hydrogen, straight-chain or branched alkyl with 1 to 6 carbon atoms, (especially methyl or ethyl), or a sodium, potassium or ammonium cation;

or straight-chain or branched alkyl with 1 to 6 carbon atoms, phenyl or benzyl, each of these radicals being optionally substituted by hydroxyl, cyano, COOR¹ or

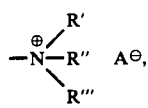

in which R¹ represents hydrogen, straight-chain or branched alkyl with 1 to 6 carbon atoms, one equivalent of a sodium, potassium, calcium, magnesium, manganese, copper, molybdenum, zinc or iron cation or an ammonium cation in which one or more hydrogen atoms can be replaced by alkyl with 1 to 6 carbon atoms (especially by methyl); R', R" and R'", independently of one another, each represent hydrogen or alkyl with 1 to 4 carbon atoms (especially methyl) and A⁻ represents chloride, bromide, iodide or methosulfate.

The outstanding activity of the ferrocenes (I) in supplying plants with iron is to be regarded as very surprising since it was to be assumed, in the light of the known state of the art, that the ferrocenes would only be of poor suitability for the stated purpose because, compared with the aminopolycarboxylic acids, they contain iron in a very powerfully complexed form. Contrary to expectations, however, the ferrocenes possess an activity, in micro-nutrient fertilization, which is better or at least equally as good as that of the iron chelate complexes of aminopolycarboxylic acids, which are the nearest compounds of the same type of action. It is particularly advantageous that the substances to be used according to the invention do not form stable complexes with the heavy metal ions of cadmium, lead and mercury present in the soil; hence, a use of ferrocene derivatives for supplying plants with iron is also safe on toxocological grounds.

In addition, the ferrocene derivatives to be used according to the invention are not only able to ensure an outstanding supply to the plant view the roots but, in contrast to all of the iron complexes described hitherto, are also able to provide an extremely efficient supply of iron by application to the leaves and in this way, which was not made possible hitherto, contribute to plant nutrition and to the prevention and cure of iron deficiency diseases in plants. The present invention thus represents a valuable enrichment of the art.

The following may be mentioned as individual examples of the ferrocene derivatives of the formula (I) which can be used according to the invention; ferrocenecarboxylic acid, sodium ferrocenecarboxylate, potassium ferrocenecarboxylate, magnesium ferrocenecarboxylate, zinc ferrocenecarboxylate, iron ferrocenecarboxylate, ammonium ferrocenecarboxylate, ferrocenecarboxylic acid methyl ester, ferrocenecarboxylic acid ethyl ester, ferrocenecarboxylic acid n-propyl ester, ferrocenecarboxylic acid i-propyl ester, ferrocenecarboxylic acid n-butyl ester and ferrocenecarboxylic acid isobutyl ester, formylferrocene and its oxime, oxime-O-methyl ether, oxime-O-ethyl ether, sodium oximate, potassium oximate, ammonium oximate, semicarbazone, thiosemicarbazine and hydrazone of the 1-amino-1,3,4-triazole, acetylferrocene and its oxime, oxime-O-methyl ether, oxime-O-ethyl ether, sodium oximate, potassium oximate, ammonium oximate, semicarbazone and thiosemicarbazone, propionylferrocene and its oxime, oxime-O-methyl ether, oxime-O-ethyl ether, sodium oximate, potassium oximate, ammonium oximate, semicarbazone and thiosemicarbazone, n-butyroylferrocene and its oxime, oxime-O-methyl ether, oxime-O-ethyl ether, sodium oximate, potassium oximate, ammonum oximate semicarbazone and thiosemicarbazone, benzoylferrocene and its oxime, oxime-O-methyl ether, oxime-O-ethyl ether, sodium oximate, potassium oximate, ammonium oximate, semicarbazone and thiosemicarbazone, o-carboxybenzoylferrocene and its sodium, potassium and ammonium salt as well as its methyl ester, β-carboxypropionylferrocene and its sodium, potassium and ammonium salt as well as its methyl ester, β-carboxypropenylferrocene and its sodium, potassium and ammonium salt as well as its methyl ester, β-carboxybutyroylferrocene and its sodium, potassium and ammonium salt as well as its methyl ester, β-carboxycyclohexylferrocene and its sodium, potassium and ammonium salt as well as its methyl ester, β-carboxycyclohexenylferrocene and its sodium, potassium and ammonium salt as well as its methyl ester, sulfoferrocene and its hydrate, sulfonamidoferrocene and its hydrate, ethylferrocene, n-propylferrocene, i-propylferrocene, n-butylferrocene, i-butylferrocene, ferroceneacrylic acid and its sodium, potassium and ammonium salt as well as its methyl ester, ferrocenehydracylic acid and its sodium, potassium and ammonium salt as well as its methyl ester, ferroceneacetonitrile, ferroceneacetic acid and its sodium, potassium and ammonium salt as well as its methyl ester, ferrocenylmethyltrimethyl-ammonium iodide, ferrocenylmethyl-trimethyl-ammonium methosulfate, ferrocenylmethanol, 1-ferrocenylethanol, 1-ferrocenyl-n-propanol, 1-ferrocenyl-n-butanol and p-hydroxyphenyl-ferrocene and its sodium and potassium salt as well as its acetate.

Some of the ferrocene derivatives of the formula (I) which can be used according to the invention are known (see "Organic Reactions", Volume 17, Chapter 1, page 1 to 151). However, the use of these derivatives for supplying plants with iron is new.

Some of the ferrocene derivatives which can be used according to the invention have not been described hitherto in the literature; however, they can be prepared in a simple manner according to processes which are known in principle.

The ferrocene derivatives of the formula (I) which can be used according to the invention are obtained, for example, when a. ferrocenecarboxylic acid or ferrocenesulfonic acid is converted into its salt, esters or amides by customary methods or when b. ferrocene is reacted with N-methyl-formanilide and phosphorus oxychloride at temperatures between 50° C and 100° C or when c. ferrocene is reacted with an acyl chloride of the general formula $$R^2\text{-CO-Cl} \quad \text{(II)},$$

in which
R² has the above-mentioned meaning, or with an acid anhydride of the general formula

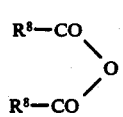

(III), in which
R⁸ represents alkyl.
at temperatures between 0° C and 100° C, optionally in the presence of a solvent, such as, for example, methylene chloride, and also in the presence of a Friedel-Crafts catalyst, such as, for example, aluminium chloride, zinc chloride, boron trifluoride, hydrogen fluoride or phosphoric acid, or when d. a ferrocene derivative of the general formula

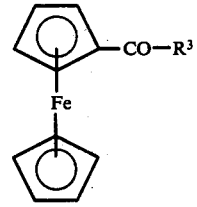

(IV), in which
R³ has the above-mentioned meaning, is reacted with an amine of the general formula $$H_2N\text{-}R^4 \quad \text{(V)},$$

in which
R⁴ has the above-mentioned meaning, in the presence of a solvent, such as, for example, ethanol, at temperatures between 0° and 150° C, preferably between 20° C and 100° C, or when e. ferrocene is reacted with a formaldehyde animal of the general formula

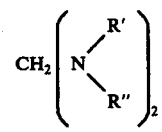

(VI), in which
R' and R'' have the above-mentioned meanings, in the presence of a solvent, such as, for example, acetic acid, and also in the presence of a catalyst, such as, for example, phosphoric acid, and the compounds thus obtained are reacted with a hydrogen halide, an alkyl halide or dimethyl sulphate, or when f. a ferrocene derivative obtained according to process variant (e) above is reacted with water or with potassium cyanide and optionally subsequently saponified, or when g. a ferrocene ketone of the general formula

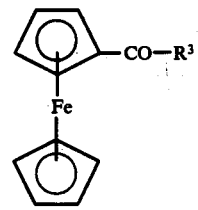

(VII), in which
R² has the above-mentioned meaning, obtained according to process variant (c) above is reduced according to customary methods.

The ferrocene derivatives of the formula (I) which can be used according to the invention are outstandingly suitable for supplying plants with the micro-nutrient iron. They can be used with particular advantage for fertilizing via the leaves since they can be absorbed well by the leaves. The ferrocene derivatives of the formula (I) can therefore be employed for preventing and for curing iron deficiency diseases in plants. In many cases it is possible to achieve a successful cure even when the disease is in an advanced stage.

The plants which are prone to iron deficiency diseases (iron deficiency chloroses) include species of cereals (for example rice, maize and millet), tuber and root crops (for example sugar beet), oleaginous fruits (for example soy bean, groundnut, olive and sunflower), table fruit (for example peach, pear, apple, apricot, plum, cherry, quince, citrus fruit, grape, hazelnut, walnut, currant, gooseberry, raspberry, blackberry, bilberry, pineapple and avocado), vegetables (for example lettuce, broad bean, pea, tomato and melon), decorative trees and shrubs (for example rose, eucalyptus, liquidambar mimosa, elm, catalpa, spirea, pyracantha, junipetr, ligustrum, hibiscus, syringa and hydragnea), perennials (for example delphinium, primula, penony, papaver, antirrhinum, iris and lupin), pot plants and annuals (for example pelargonium, petunia, gardenia, calceolaria, chrysanthemum, camellia and begonia), peat-loving plants (for example azalea, rhododendron, erica and skimmia) and grasses (for example lawn grases).

The active compounds to be used according to the present invention can be converted into he usual formulations, such as solutions, emulsions, suspensions, powders, pastes and granulates. These may be produced in known manner, for example by mixing the active compounds with extenders, that is, liquid or solid or liquefied gaseous diluents or carriers, optionally with the use of surface-active agents, that is, emulsifying agents and/or dispersing agents and/or foam-forming agents. In the case of the use of water as an extender, organic solvents can, for example, also be used as auxiliary solvents.

As liquid diluents or carriers, there are preferably used aromatic hydrocarbons, such as xylenes, toluene, benzene or alkyl naphthalenes, chlorinated aromatic or aliphatic hydrocarbons, such as chlorobenzenes, chloroethylenes or methylene chloride, aliphatic hydrocarbons, such as cyclohexane or paraffins, for exaple mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethyl formamide, dimethyl sulfoxide or acetonitrile, as well as water.

By liquefied gaseous diluents or carriers are meant liquids which would be gaseous at normal temperatures and pressures, for example aerosol propellants, such as halogenated hydrocarbons, for example freon.

As solid diluents or carriers, there are preferably used ground naturl minerals, such as kaolins, clays, talc, chalk, quartz, attapulgite, montmorillonite or diatomaceous earth, r ground synthetic minerals, such as highly-disperesed silicic acid, alumina or silicates.

Preferred examples of emulsifying and foam-forming agents include non-ionic and anionic emulsifiers, such as polyoxyethylene-fatty acid esters, polyoxyethylene-fatty alcohol ethers, for example alkylarlypolyglycol ethers, alkyl sulfonates, alkyl sulfates and aryl sulfonates as well as albumin hydrolyzation products; and preferred examples of dispersing agents include lignin sulfite waste liquors and methyl cellulose.

The compounds to be used according to the invention for supplying plants with iron can be present in the formulations as a mixture with other fertilizers or pesticidally active compounds.

The formulations in general contain from 0.1 to 95 percent by weight of active compound, preferably from 0.5 to 90 percent by weight.

The active compounds can be used as such, in the form of their formulations or as the use forms prepared therefrom, such as ready-to-use solutions, emulsions, foams, suspensions, powders, pastes and granules. They may be used in accorddance with the methods customary in agriculture and in horticulture, for example by direct introduction into the soil, by watering, spraying, atomizing, scattering or dusting. The following may be mentioned as special types of application: root application, leaf application, stem injection and bark application. In the case of root application, the fertilizer can neither be mixed with the culture substrate or be introduced into furrows in the soil. Furthermore it is possible to introduce the fertilizer into the lower root region by means of a fertilizer lance or through punched or drilled holes. Application to the leaf is as a rule effected by spraying the plants with a fertilizer solution or dipping plants or parts of plants into a fertilizer solution. In the case of stem injection, the fertilizer is directly introduced into the plants through bore-holes on tree trunks or branches. Bark application can be effected by spraying the bare wood with the fertilizer solution, or by placing bands, or paper, textile or foam plastic, impregnated with nutrients, on tree trunks or branches — if appropriate after partial or complete removal of the layer of bark or cork in the treatment zone. Application to the bark by means of pastes containing nutrient is also possible.

It is also possible to apply the ferrocene derivatives in accordance with the ultra-low-volume (ULV) method. Furthermore, those ferrocene derivatives which contain ionic groups can be absorbed on ion exchangers and employed in this form as fertilizers.

The amount of the ferrocene derivatives (I) which is employed can be varied within a fairly wide range. It depends essentially on the nature of the soil and on the nutrient requirement of the particular plant. In general, the amounts of active compound used are between 0.1 and 100 kg/ha and preferably between 1 and 50 kg/ha.

The present invention also provides means of yielding crops which have been grown in areas in which immediately prior to and/or during the time of the growing, a ferrocene of the formula (I) was applied alone or in admixture with a diluent or carrier.

The good activity of the ferrocene derivatives to be used according to the invention in supplying plants with iron can be seen from the biotest Examples which follow. in the tables accompanying these Examples, the ferrocenes of the formula (I) are each identified by the number (given in parenthesis) of the corresponding preparative Example hereinafter.

EXAMPLE A

COMBATING IRON DEFICIENCY/ROOT UPTAKE TEST

Test plant: chrysanthemum indicum (Variety: Yellow Delaware)
Culture substrate: Mixture of polystyrene foam flock (Styromull) and potassium alginate in the volume ratio of Test plants were grown in a culture substrate of the above-mentioned composition, fertilization and watering being effected by adding, twice weekly, a mineral iron deficiency nutrient solution according to Hoagland and Arnon (Circular 347, College of Agriculture, University of California, Berkeley 1950). The completely chlorotic test plants grown in this way were transplanted, at the five-leaf stage, into another culture substrate of the above-mentioned composition, to which, however, the particular desired amount of iron fertilizer had been admixed. During the further growth, fertilization and watering were effected in the same way as during the initial growth.

The evaluation was made when an average of 5 leaves had newly formed on the plants treated with an optimum amount of a water-soluble, commercially available iron fertilizer. In each case the average number of newly formed leaves was determined on all the test plants. Furthermore, the intensity of the green color of newly formed leaves was rated and expressed on a numerical scale. In this, the figures denote:

1 = 0% chlorotic (dark green)
3 = 25% chlorotic
5 = 50% chlorotic
7 = 75% chlorotic
9 = 100% chlorotic (corresponding to the untreated control plants)

The active compounds, the active compound concentrations and the experimental results can be seen from the table which follows. In this and subsequent tables, "Sequestrene 138 Fe" refers to a commercially available iron fertilizer based on an iron chelate complex of ethylenediamine-N-N'-di-(o-hydroxyphenyl)-acetic acid.

EXAMPLE B

Combating iron deficiency/root uptake test

Test plant: Chrysanthemum indicum (Variety: Yellow Delaware)
Culture substrate: Mixture of polystyrene foam flock (Styromull) and potassium alginate in the volume ratio of 10:1.

Test plants were grown in a culture substrate of the above-mentioned composition, fertilization and watering being effected by adding, twice weekly, a mineral iron deficiency nutrient solution according to Hoagland and Arnon (circular 347, college of Agriculture, University of California, Berkeley 1950). The completely chlorotic test plants grown in this way were transplanted, at the five-leaf stage, into another culture substrate of the above-mentioned composition, to which, however, the particular desired amount of iron fertilizer had been admixed. During the further growth, fertilization and watering were effected in the same way as during the initial growth.

The evaluation was made when an average of 5 leaves had newly formed on the plants treated with an optimum amount of a water-soluble, commercially available iron fertilizer. In each case the average number of newly formed leaves was determined on all the test plants. Furthermore, the intensity of the green color of newly formed leaves was rated and expressed on a numerical scale. In this, the figures denote:

1 = 0% chlorotic (dark green)
3 = 25% chlorotic
5 = 50% chlorotic
7 = 75% chlorotic
9 = 100% chlorotic (corresponding to the untreated control plants)

The active compounds, the active compound concentrations and the experimental results can be seen from the table which follows.

Table A

Combating iron deficiency/root uptake test
Test plant: Chrysanthemum indicum/Variety: Yellow Delaware

| Nutrient preparation | Water solubility of the preparation | Nutrient preparation concentration in the substrate [mg/l] | Iron concentration in the substrate [mg/l] | Intensity of the green color of young leaves | Average number of newly formed leaves | Notes |
|---|---|---|---|---|---|---|
| — (Control) | — | — | — | 9 | 0 | |
| $FeSO_4 \cdot 7H_2O$ (known) | complete | 15 | 3 | 9 | 0 | |
| Sequestrene 138 Fe (known) | complete | 50 | 3 | 2 | 5 | |
| (2) | complete | 120 | 3 | 1 | 6 | |
| (22) | complete | 131 | 3 | 1 | 1 | additional stunting effect |
| (3) | complete | 60 | 3 | 1 | 5 | |
| (28) | complete | 50 | 9.3 | 2 | 4 | |
| (4) | complete | 50 | 11.3 | 1 | 7 | |

Table B

Combating iron deficiency/root uptake test
Test plant: Chrysanthemum indicum/Variety: Yellow Delaware

| Nutrient preparation | Water solubility of the preparation | Nutrient preparation concentration in the substrate [mg/l] | Iron concentration in the substrate [mg/l] | Intensity of the green color of young leaves | Average number of newly formed leaves | Notes |
|---|---|---|---|---|---|---|
| — (control) | — | — | — | 9 | 0 | |
| Sequestrene 138 Fe (known) | complete | 50 | 3 | 2 | 5 | |
| (29) | slight | 62 | 15 | 1 | 6 | |

Table B-continued

Combating iron deficiency/root uptake test
Test plant: Chrysanthemum indicum/Variety: Yellow Delaware

| Nutrient preparation | Water solubility of the preparation | Nutrient preparation concentration in the substrate [mg/l] | Iron concentration in the substrate [mg/l] | Intensity of the green color of young leaves | Average number of newly formed leaves | Notes |
| --- | --- | --- | --- | --- | --- | --- |
| (1) | slight | 52 | 15 | 1 | 5 | |
| (8) | slight | 123 | 30 | 1 | 1 | additional stunting effect |
| (16) | slight | 29.9 | 3 | 1 | 4 | |
| (30) | slight | 57.7 | 15 | 1 | 3 | |
| (13) | slight | 154 | 30 | 1 | 6 | |
| (15) | slight | 151 | 30 | 1 to 2 | 5 | |
| (11) | slight | 123 | 30 | 1 | 4 | |

EXAMPLE C

Combating iron deficiency/root uptake test

The active compounds, the active compound concentrations and the experimental results can be seen from the table which follows.

Table C

Combating iron deficiency/root uptake test
Test plant: Vine/Variety: Muller Thurgau

| Nutrient preparation | Water solubility of the preparation | Nutrient preparation concentration in the substrate [mg/l] | Iron concentration in the substrate [mg/l] | Intensity of the green color of young leaves | Average number of newly formed leaves | Notes |
| --- | --- | --- | --- | --- | --- | --- |
| — (control) | — | — | — | 9 | 0 | |
| $FeSO_4 \cdot 7H_2O$ (known) | complete | 15 | 3 | 9 | 0 | |
| Sequestrene 138 Fe (known) | complete | 50 | 3 | 3 | 1 | |
| (2) | complete | 120 | 3 | 2 | 4 | |
| (3) | complete | 120 | 6 | 2 | 5 | |

Test Plant: Vine (variety: Müller Thurgau)
Culture substrate: Mixture of polystyrene foam flock (Styromull) and potassium alignate in the volume ratio of 10:1.

Test plants were grown in a culture substrate of the above-mentioned composition, fertilization and watering being effected by adding, twice weekly, a mineral iron deficiency nutrient solution according to Hoagland and Arnon (Circular 347, College of Agriculture, University of California, Berkeley 1950). The completely chlorotic test plants grown in this way were transplanted, at the five-leaf stage, into another culture substrate of the above-mentioned composition, to which, however, the particular desired amount of iron fertilizer had been admixed. During the further growth, fertilization and watering were effected in the same way as during the initial growth.

The evaluation was made when an average of 1 leaf had newly formed on the plants treated with an optimum amount of water-soluble, commercially available iron fertilizer In each case the average number of newly formed leaves was determined on all the test plants. Furthermore, the intensity of the green color of newly formed leaves was rated and expressed on a numerical scale. In this, the figures denote:

1 = 0% chlorotic (dark green)
3 = 25% chlorotic
5 = 50% chlorotic
7 = 75% chlorotic
9 = 100% chlorotic (corresponding to the untreated control plants)

Example D

Combating iron deficiency / root uptake test

Test plant: Vine (variety: Müller Thurgau)
Culture substrate: Mixture of polystyrene foam flock (Styromull) and potassium alginate in the volume ratio of 10:1

Test plants were grown in a culture substrate of the above-mentioned composition, fertilization and watering being effected by adding, twice weekly, a mineral iron deficiency nutrient solution according to Hoagland and Arnon (Circular 347, College of Agriculture, University of California, Berkely 1950). The completely chlorotic test plants grown in this way were transplanted, at the five-leaf stage, into another culture substrate of the above-mentioned composition, to which, however, the particular desired amount of iron fertilizer had been admixed. During the further growth, fertilization and watering were effected in the same way as during the initial growth.

The evaluation was made when an average of 1 leaf had newly formed on the plants treated with an optimum amount of a water-soluble, commercially available iron fertilizer. In each case the average number of newly formed leaves was determined on all the test plants. Furthermore, the intensity was rated and expressed on a numerical scale. In this, the figures denote:

1 = 0% chlorotic (dark green)
3 = 25% chlorotic
5 = 50% chlorotic
7 = 75% chlorotic
9 = 100% chlorotic (corresponding to the untreated control plants)

The active compounds, the active compound concentrations and the experimental results can be seen from the table which follows:

Table D

Combating iron deficiency/root uptake test
Test plant: Vine/Variety: Muller/Thurgau

| Nutrient preparation | Water solubility of the preparation | Nutrient preparation concentration in the substrate [mg/l] | Iron concentration in the substrate [mg/l] | Intensity of the green color of young leaves | Average number of newly formed leaves | Notes |
|---|---|---|---|---|---|---|
| — (control) | — | — | — | 9 | 0 | |
| FeSO$_4$ . 7H$_2$O (known) | complete | 15 | 3 | 9 | 0 | |
| Sequestrene 138 Fe (known) | complete | 50 | 3 | 3 | 1 | |
| (29) | slight | 123 | 30 | 2 | 5 | |
| (1) | slight | 104 | 30 | 2 | 4 | |
| (8) | slight | 123 | 30 | 2 | 7 | |
| (16) | slight | 302 | 30 | 2 | 5 | |
| (30) | slight | 115 | 30 | 2 | 6 | |

EXAMPLE E

Combating iron deficiency/leaf uptake test

Test plant: Chrysanthemum indicum (Variety: Yellow Delware)
culture substrate    Mixture of polystyrene foam flock (Styromull) and potassium alginate in the volume ratio of 10:1

To prepare a suitable fomulation of the active compound, the particular amount of active compound desired was dissolved in water. In the case of active compounds which have a low solubility in water the active compound formulation was prepared by dissolving 1 g of the active compound in 10 ml of a formulation mixture (FM) consisting of 47 parts by volume of dimethylformamide, 47 parts by volume of acetone and 6 parts by volume of an alkylaryl polyglycol ether (emulsifier) and then diluting the concentrate, thus obtained, with water to the desired concentration.

Test plants were grown in a culture substrate of the above-mentioned composition, fertilization and watering being effected by adding, twice weekly, a mineral iron deficiency nutrient solution according to Hoagland and Arnon (Circular 347, College of Agriculture, University of California, Berkeley 1950). The completely chlorotic test plants grown in this way, in the five-leaf stage, were sprayed with the active compound formulation until dripping wet, using covers to ensure that the active compound formulation did not enter the culture substrate. After 2 days the plants were again sprayed with the active compound formulation in the same manner.

The evaluation took place when an average of 2 leaves had newly formed on the plants treated with an optimum amount of a water-soluble, commercially available iron fertilizer. In each case, the average number of newly formed leaves was determined on all test plants. Furthermore, the intensity of the green color of newly formed leaves was rated and expressed on a numerical scale.

In this, the figures denote:
1 = 0% chlorotic (dark green)
3 = 25% chlorotic
5 = 50% chlorotic
7 = 75% chlorotic
9 = 100% chlorotic (corresponding to the untreated conrol plants)

The active compounds, the active compound concentrtions and the experimental results can be seen from the table which follows. In this and subsequent tables, "Fetrilon" refers to a commercially available iron fertilizer based on an iron chelate complex of the sodium salt of ethylenediamine-tetraacetic acid.

Table E

Combating iron deficiency/leaf uptake test
Test plant: Chrysanthemum indicum/Variety: Yellow Delaware

| Nutrient preparation | Water solubility of the preparation | Nutrient preparation in the spray liquor [%] | Iron concentration in the spray liquor [ppm] | Intensity of the green color of young leaves | Average number of newly formed leaves |
|---|---|---|---|---|---|
| — (control) | — | — | — | 9 | 0 |
| Fetrilon (known) | complete | 0.2 | 100 | 3 | 2 |
| (2) | complete | 0.4 | 100 | 1 | 8 |
| (22) | complete | 0.44 | 100 | 2 | 4 |
| (29) | slight | 0.1 | 250 | 2 | 7 |
| (8) | slight | 0.1 | 250 | 1 | 6 |
| (11) | slight | 0.5 | 1,250 | 1 | 7 |

EXAMPLE F

Combating deficiency/leaf deficiency uptake test

Test plant: Vine (Variety: Müller Thurgau)
Culture substrate: Mixture of polystyrene foam flock (Styromull) and potassium alginate in the volume ratio of 10:1

To prepare a suitable formulation of the active compound, the particular amount of active compound desired was dissolved in water. In the case of active compounds which have a low solubility in water the active compound formulations was prepared by dissolving 1 g of the active compound in 10 ml of a formulation mixture (FM) consisting of 47 by volume of dimethylformamide, 47 parts by volume of acetone and 6 parts by volume of an alkylaryl polyglycol ether (emulsifier) and then diluting the concentrate, thus obtained, with water to the desired concentration.

Test plants were grown in a culture substrate of the above-mentioned composition, fetilization and watering being effected by adding, twice weekly, a mineral iron deficiency nutrient solution according to Hoagland and Arnon (Circular 347, College of Agriculture, University of California, Berkeley 1950). The completely chlorotic test plants grown in this way, in the five-leaf stage, were sprayed with the active compound formulation until dripping wet, using covers to ensure that the active compound formulation did not enter the culture substrate. After 2 days the plants were again sprayed with the active compound formulation in the same manner.

The evaluation took place when an average of 1 leaf had newly formed on the plants treated with an optimum amount of a water-soluble commercially available iron fertilizer. In each case, the average number of newly formed leaves was determined on all test plants. Furthermore, the intensity of the green color of newly formed leaves was rated and expressed on a numerical scale.

in this, the figures denote:

1 = 0% chlorotic (dark green)
3 = 25% chlorotic
5 = 50% chloritic
7 = 75% chlorotic
9 = 100% chlorotic (corresponding to the untreated control plants).

The active compounds, the active compound concentrations and the experimental results can be seen from the table which follows.

Table F

| | Combating iron deficiency/leaf uptake test Test plant: Vine/Variety: Muller Thurgau | | | | |
|---|---|---|---|---|---|
| Nutrient preparation | Water solubility of the preparation | Nutrient preparation in the spray liquor [%] | Iron concentration in the spray liquor [ppm] | Intensity of the Average green color of young leaves | Average number of newly formed leaves |
| — | — | — | — | 9 | 0 |
| (control Fetrilon (known) | complete | 0.2 | 100 | 3 | 1 |
| (2) | complete | 0.4 | 100 | 2 | 5 |
| (3) | complete | 0.2 | 100 | 2 | 3 |
| (29) | slight | 0.1 | 250 | 2 | 4 |
| (8) | slight | 0.5 | 1,250 | 1 | 6 |
| (11) | slight | 0.7 | 1,250 | 2 | 5 |

The preparation of the ferrocene derivatives to be used according this invention is illustrated by the following preparative Examples.

EXAMPLE 1

(1)

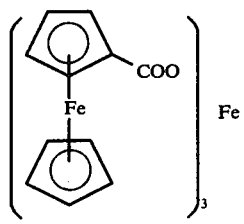

9.9 g (0.043 mole) of ferrocenecarboxylic acid were added to a solution of 1.7 g (0.043 mole) of sodium hydroxide in 100 ml of water at room temperature, while stirring, and a solution of 3.9 g (0.0143 mole) of iron (III) chloride hexahydrate in 30 ml of water was then added. A grey precipitate was deposited and, after the mixture had been stirred for two hours, this precipitate was filtered off, washed and dried. In this way 9.8 g (almost 100% of theory) of iron ferrocenecarboxylate which had a melting point of above 300° C were obtained.

Elementary analysis:

$C_{33}H_{27}O_6Fe_4$ (742.97) Calculated: 53.35% C; 3.66% H; Found: 52.7 % C; 3.9 % H.

The compounds listed in Table 1 which follows were obtained by procedures analogous to that of Example 1.

Table 1

(I)

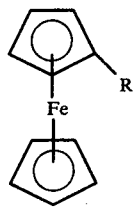

| Example No. | R | Melting point [° C] |
|---|---|---|
| 2 | $-COO^{\ominus}Na^{\oplus}$ | above 300 |
| 3 | $-COO^{\ominus}K^{\oplus}$ | above 300 |
| 4 | $-COO^{\ominus}\overset{\oplus}{N}H_4$ | above 195 (decomposition) |
| 5 | $-COO^{\ominus}\dfrac{Mg^{2\oplus}}{2}$ | above 300 |
| 6 | $-COO^{\ominus}\dfrac{Zn^{2\oplus}}{2}$ | above 300 |

EXAMPLE 7

(7)

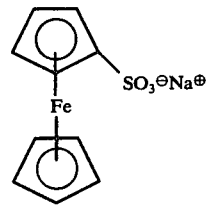

The sodium salt of ferrocenesulfonic acid was prepared by a procedure analogous to that in Example 1, starting from ferrocenesulfonic acid and sodium hydroxide.

EXAMPLE 8

(8)

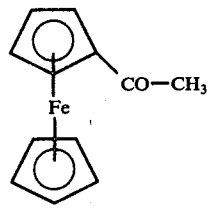

A mixture of 93.0 g (0.5 mole) of ferrocene, 250 ml of acetic anhydride and 20 ml of 85% strength phosphoric acid was heated to 100° C for 10 minutes, then cooled and poured onto ice. After leaving the mixture to stand overnight, the solid residue was filtered off and washed with water. For further purification the residue was dissolved in cyclohexane, while warming, and animal charcoal/Tonsil were added. The mixture was then filtered and the filtrate was evaporated to dryness under reduced pressure. In this way 64 g (55.4% of theory) of acetylferrocene with a melting point of 84 to 86° C were obtained.

The compounds mentioned in Examples 9 and 10 were obtained by procedures analogous to that in Example 8:

EXAMPLE 9

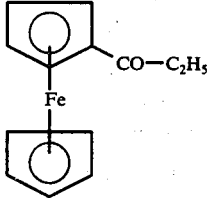 (9)

Yield: 45% of theory
Boiling point: 132–136° C/4 mm Hg

EXAMPLE 10

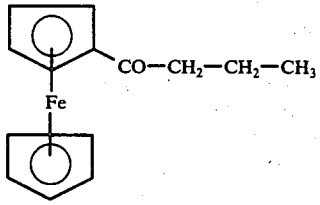 (10)

Yield: 49% of theory
Melting point: 35–38° C
Boiling point: 140° C/3 mm Hg

EXAMPLE 11

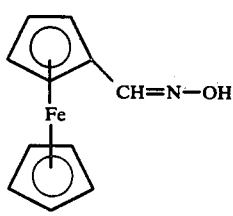 (11)

A solution of 12 g (0.3 mole) of sodium hydroxide in 20 ml of water was added dropwise, while cooling, to a suspension of 20.9 g (0.3 mole) of hydroxylamine hydrochloride in 200 ml of ethanol and a solution of 42.8 g (0.2 mole) of ferrocenealdehyde in 200 ml of ethanol was then added. After boiling for 5 hours under reflux, the reaction mixture was cooled. The undissolved constitutents were filtered off, the filtrate was concentrated to dryness, the residue was suspended in water, the suspension was filtered and the product was dried. In this way 42 g (91.7% of theory) of ferrocenealdoxime with a melting point of 228° C were obtained.

The compounds listed in Table 2 which follows were obtained by procedures analogous to that in Example 11.

Table 2

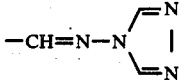 (I)

| Ex. No. | R | Melting point [° C] |
|---|---|---|
| 12 | —CH=N—NH—CO—NH$_2$ | 225 (decomposition) |
| 13 | —CH=N—NH—CS—NH$_2$ | 185 |
| 14 | —C=N—NH—CS—NH$_2$<br>   \|<br>   CH$_3$ | 148–154 (decomposition) |
| 15 | —CH=N—N⟨=N / =N⟩ | >170 (decomposition) |
| 16 | —CH=NCH$_2$CH$_2$N=CH— (ferrocenyl) | 154 (decomposition) |

The compound listed in Table 3 which follows were prepared by customary reactions, starting from ferroceneoximes.

Table 3

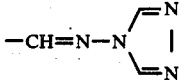 (I)

| Ex. No. | R | Melting point [° C] |
|---|---|---|
| 17 | —CH=N—O$^{\ominus}$Na$^{\oplus}$ | >180 (decomposition) |
| 18 | —CH=N—OCH$_3$ | 45–48 (decomposition) |
| 19 | —CH=N—OC$_2$H$_5$ | 173 |
| 20 | —CH=N—O—CO—NH—CH$_3$ | 105 |

EXAMPLE 21

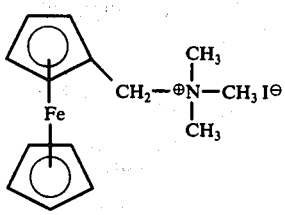 (21)

173 g (1.69 moles) of bis-dimethylaminomethane were added, while cooling, to a solution of 173 g of phosphoric acid in 1,600 ml of glacial acetic acid, 185.6 g (1.0 mole) of ferrocene were then added and the mixture was warmed for 5 hours under a nitrogen atmosphere on a waterbath. The reaction mixture was then cooled to room temperature and diluted with 2,200 ml of water and unconverted ferrocene was removed by extraction with ether. The remaining reaction mixture was rendered alkaline by adding 480 g of sodium hydroxide, diluted with a further 800 ml of water and then extracted three times with ether. The organic phase was separated off, washed with water and, after drying over sodium sulfate, concentrated. 204 g (89% of theory) of N,N-dimethylamino-methylferrocene remained and were taken up in 215 ml of methanol. 215 ml (500 g) of methyl iodide were added to the resulting solution and the mixture was heated for 5 minutes on a boiling waterbath and, after cooling to room temperature, poured into 3,200 ml of ether. The product, which was initially obtained as an oil, crystallised on trituration. In this way, 323 g (83.9% of theory) of N,N-dimethylamnio-methylferrocene methoiodide with a melting point of 213° C (decomposition) were obtained.

EXAMPLE 22

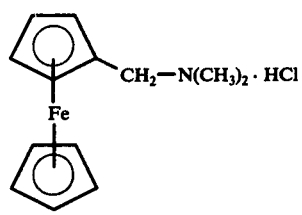

(22)

N,N-Dimethylamnio-methylferrocene hydrochloride was obtained by reacting N,N-dimethylamino-methyl-ferrocene with hydrochloric acid.

EXAMPLE 23

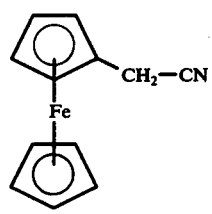

(23)

58 g (0.15 mole) of N,N-dimethylamino-methylferrocene methoidoide were added to a solution of 57 g (0.88 mole) of potassium cyanide in 570 ml of water and the mixture was heated to the boil, whereupon the solid dissolved. The evolution of trimethylamine started within a few minutes, while at the same time an oil which was volatile with steam separated out. After stirring for two hours under reflux, the mixture was cooled to room temperature, whereupon the oily product solidified. The solid was separated off and the residual solution was extracted with ether. The combined organic phases were washed with water and, after drying over sodium sulfate, concentrated under reduced pressure. The residue was recrystallized from 200 ml of hexane. In this way 26 g (76.9% of theory) of cyanomethylferrocene with a melting point of 82° to 83° C were obtained.

EXAMPLE 24

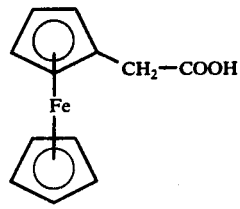

(24)

Melting point: 150–152° C

Carboxymethylferrocene was obtained by saponification of cyanomethylferrocene.

EXAMPLE 25

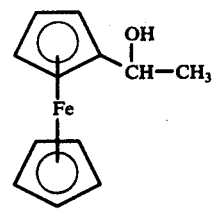

(25)

A solution of 46.2 g (0.2 mole) of acetylferrocene in 200 ml of ethanol was added dropwise, at room temperature, to a solution of 30.4 g (0.8 mole) of sodium borohydride in 200 ml of water. The reaction mixture was stirred overnight at room temperature and poured into water and the solid obtained was filtered off. The product was washed and dried. In this way, 40 g of 1-hydroxyethylferrocene with a melting point of 69° C were obtained.

EXAMPLE 26

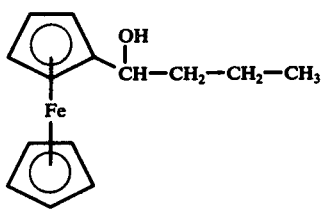

(26)

1-Hydroxy-n-butyl-ferrocene was obtained by a procedure analogous to that in Example 25 by reacting n-butyroylferrocene with sodium borohydride. Melting point: 30–35° C

EXAMPLE 27

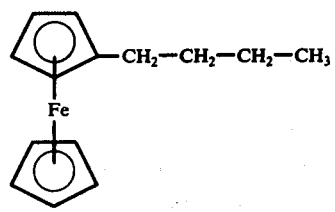

(27)

n-Butylferrocene was prepared by reducing n-butyroylferrocene. Boiling point: 130° C/2-3 mm Hg.

EXAMPLES 28-30

The following ferrocene derivatives can be prepared by customary methods.

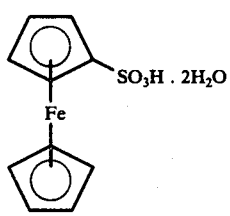 (28)

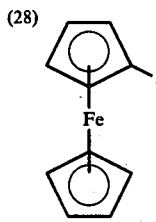 (29)

 (30)

It will be understood that the specification and examples are illustrative but not limitative of the present invention and that other embodiments within the spirit and scope of the invention will suggest themselves to those skilled in the art.

What is claimed is:

1. A method of supplying plants with the micro-nutrient iron, which comprises applying to the plants or to a plant habitat plant-nutritionally effective amounts of a ferrocene derivative of the general formula

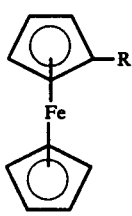 (I)

in which
R represent the group $COOR^1$,
in which
R$^1$ is hydrogen, alkyl, one equivalent of an alkali metal, alkaline earth metal or heavy metal cation, or an ammonium cation in which one or more hydrogen atoms can be replaced by alkyl, or
R represent the group $COR^2$,
in which
R$^2$ is alkyl, substituted alkyl, alkenyl, substituted alkenyl, cycloalkyl, substituted cycloalkyl, cycloalkenyl, substituted cycloalkenyl phenyl or substituted phenyl, or

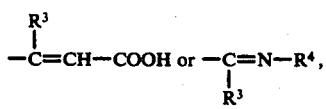

in which
R$^3$ is hydrogen or alkyl, and
R$^4$ is a ureido or thioureido radical, a radical of the formula —CH$_2$—CH$_2$—N=CH-ferrocene, a 5-membered or 6-membered heterocyclic radical or a group of the formula —OR$^5$ or —NH-R$^6$,
in which
R$^5$ is hydrogen, alkyl, one equivalent of an alkali metal or alkaline earth metal cation, or an ammonium cation in which one or more hydrogen atoms can be replaced by alkyl, and
R$^6$ is carbocyclic aryl or 5-membered or 6-membered heterocyclic radical, or
R represents the sulphonamide group or the radical —SO$_3$R$^7$,
in which
R$^7$ is hydrogen, alkyl, one equivalent of an alkali metal or alkaline earth metal cation, or an ammonium cation in which one or more hydrogen atoms can be replaced by alkyl, or
R represents an alkyl, aralkyl, aryl or aryl radical substituted by hydroxyl, cyano, COOR$^1$ or

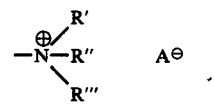

in which
R$^1$ is identified as above; and
R', R'', and R''', independently of one another, each represent hydrogen or alkyl and
A$^-$ halide or methosulphate.

2. A method according to claim 1, in which a ferrocene derivative of the general formula (I) is employed in which
R represent the COOR$^1$ group, in which
R$^1$ represents hydrogen, straight-chain or branched alkyl with 1 to 6 carbon atoms, one equivalent of a sodium, potassium, calcium, magnesium, manganese copper molybdenum, zinc or iron cation or an ammonium in which one or more hydrogen atoms can be replaced by alkyl with 1 to 6 atoms.

3. A method according to claim 1, in which a ferrocene derivative of the general formula (I) is employed in which R represents the COR$^2$ group,
in which
R$^2$ represent hydrogen, straight-chain or branched alkyl of from 1 to 6 carbon atoms, straight-chain or branched alkenyl of from 2 to 6 carbon atoms, cyclohexyl, cyclohexenyl or phenyl, each of the 5 last-mentioned radicals being optionally substituted by carboxyl, hydroxyl or the group CO-OX or OX, in which X represent one equivalent of a sodium, potassium, calcium, magnesium, manganese, copper, molybdenum, zinc or iron cation or represents alkyl with 1 to 4 carbon atoms.

4. A method according to claim 1, in which a ferrocene derivative of the general formula (I) is employed in which R represents the group —CR$^3$=CH-COOH or —CR$^3$=$^{N-R4}$, in which
R$^3$ represent hydrogen or straight-chain or branched alkyl of from 1 to 6 carbon atoms, and
R$^4$ represents a ureido or thioureido radical, a radical of the formula —CH$_2$—CH$_2$—N=CH-ferrocene, a 5-membered or 6-membered heterocyclic radical, the group OR$^5$, in which R$^5$ represents hydrogen, straight-chain or branched alkyl with 1 to 4 carbon atoms, one equivalent of a socium, potassium or calcium cation or an ammonium cation in which one or more hydrogen atoms can be replaced by alkyl with 1 to 6 carbon atoms, or the group —NH—R⁶, in which R⁶ represent phenyl or a 5-membered or 6-membered heterocyclic radical.

5. A method according to claim 1, in which a ferrocene derivative of the general formula (I) is employed in which R represents a sulphonamide group or the radical —SO₃R⁷, in which R⁷ represents hydrogen, straight-chain or branched alkyl with 1 to 6 carbon atoms, or a sodium, potassium or ammonium cation.

6. A method according to claim 1, in which a ferrocene derivative of the general formula (I) is employed in which R represents a stragith-chain or branched alkyl with 1 to 6 carbon atoms, phenyl or benzyl, each of these radicals being optionally substituted by hydroxyl, cyano, COOR¹ or

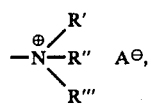

in which
R¹ represents hydrogen, straight-chain or branched alkyl with 1 to 6 carbon atoms, one equivalent of a sodium, potassium, calcium, magnesium, manganese, copper, molybdenum, zinc or iron cation or an ammonium cation in which one or more hydrogen atoms can be replaced by alkyl with 1 to 6 carbon atoms R', R" and R''', independently of one another, each represent hydrogen or alkyl with 1 to 4 carbon atoms and represents chloride, bromide, iodide or methosulphate.

7. A method according to claim 1, in which the ferrocene derivative is of the formula

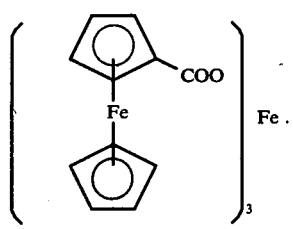

8. A method according to claim 1, in which the ferrocene derivative is of the formula

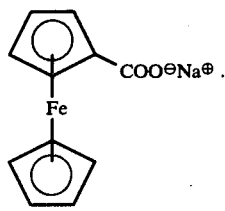

9. A method according to claim 1, in which the ferrocene derivative is of the formula

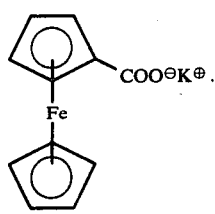

10. A method according to claim 1, in which the ferrocene derivative is of the formula

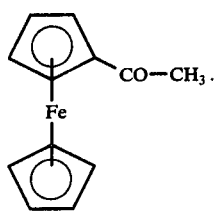

11. A method according to claim 1, in which the ferrocene derivative is of the formula

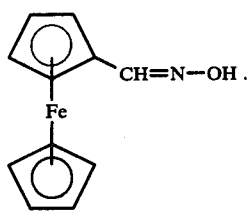

12. A method according to claim 1, in which the ferrocene derivative is of the formula

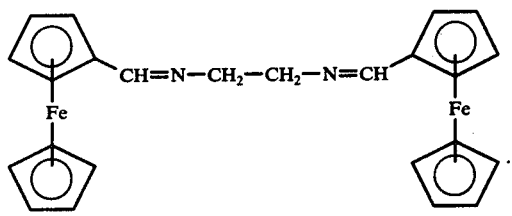

13. A method according to claim 1, in which the ferrocene derivative is of the formula 14. A method according to claim 13, in which the active ingredient is applied in an amount of between 1 and 50 kg/hectare.

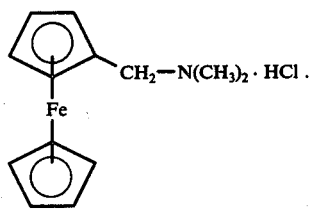

15. A method according to claim 1, in which the ferrocene derivative is of the formula

16. A method according to claim 1, in which the ferrocene derivative is of the formula
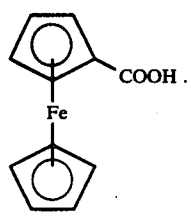
17. A method according to claim 1 in which the active ingredient is applied to an area of plant cultivation in an amount of between 0.1 and 100 kg/hectare.
18. A method according to claim 17, in which the plants are suffering from an iron-deficiency disease.
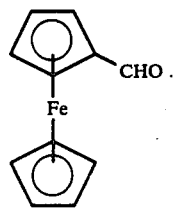

UNITED STATES PATENT AND TRADEMARK OFFICE
CERTIFICATE OF CORRECTION

PATENT NO. : 4,053,296
DATED : October 11, 1977
INVENTOR(S) : Volker Mues and Johannes Niggemann It is certified that error appears in the above-identified patent and that said Letters Patent are hereby corrected as shown below:

In the Abstract:

In the $R^7$ definition, delete, "pl" before --R--

Column 8, line 19, "neither" should read --either--;

Column 14, line 54, insert --parts-- after "47";

Column 15, line 26, delete "Average" in next to last colum, and insert --Average-- as first word in last column;

Column 19, line 20, "dimethylamnio" should read --dimethylamino--

Claim 1, column 21, line 60, after the $R^2$ definition, before equation, insert --R represents the group--

Claim 1, column 22, line 29, "A-halide" should read

--$A^{\ominus}$ represents--

Claim 1, column 22, lines 36 and 37, insert a comma(,) after "manganese, copper,"

UNITED STATES PATENT AND TRADEMARK OFFICE
CERTIFICATE OF CORRECTION

PATENT NO. : 4,053,296
DATED : October 11, 1977
INVENTOR(S) : Volker Mues and Johannes Niggemann It is certified that error appears in the above-identified patent and that said Letters Patent are hereby corrected as shown below:

Claim 4, column 22, line 58, wrong typeface used for "=N-R$^4$"

Claim 6, column 23, line 15, "stragith-chain" should read --straight-chain--

Claim 6, column 23, line 37, insert --A$^\ominus$-- before "represents"

Claims 14 to 17 are improperly numbered, i.e.,

*Signed and Sealed this*

*Eighteenth* Day of *April 1978*

[SEAL]

Attest:

RUTH C. MASON
*Attesting Officer*

LUTRELLE F. PARKER
*Acting Commissioner of Patents and Trademarks*

UNITED STATES PATENT AND TRADEMARK OFFICE
CERTIFICATE OF CORRECTION

PATENT NO. : 4,053,296
DATED : October 11, 1977
INVENTOR(S) : Volker Mues and Johannes Niggemann It is certified that error appears in the above—identified patent and that said Letters Patent are hereby corrected as shown below:

In the Abstract:

In the $R^7$ definition, delete, "pl" before --R--.

Column 8, line 19, "neither" should read --either--;

Column 14, line 54, insert --parts-- after "47";

Column 15, line 26, delete "Average" in next to last column, and insert --Average-- as first word in last column;

Column 19, line 20, "dimethylamnio" should read --dimethylamino--

Claim 1, Column 21, line 60, after the $R^2$ definition, before equation, insert --R represents the group--;

Claim 1, Column 22, line 29, "A-" should read --A$^\ominus$ represents--;

Claim 1, Column 22, lines 36 and 37, insert a comma(,) after "manganese‿ copper‿"

UNITED STATES PATENT AND TRADEMARK OFFICE
CERTIFICATE OF CORRECTION

PATENT NO. : 4,053,296
DATED : October 11, 1977
INVENTOR(S) : Volker Mues and Johannes It is certified that error appears in the above-identified patent and that said Letters Patent are hereby corrected as shown below:

Claim 4, Column 22, line 58, wrong typeface used for "$=N-R^4$"

Claim 6, Column 23, line 15, "stragith-chain" should read --straight-chain--

Claim 6, Column 23, line 37, insert --$A^{\ominus}$-- before "represents"

This certificate supersedes Certificate of Correction issued April 18, 1978.

Signed and Sealed this

First Day of May 1979

[SEAL]

Attest:

RUTH C. MASON
Attesting Officer

DONALD W. BANNER
Commissioner of Patents and Trademarks